US00PP09421P

United States Patent [19]

Pouw

[11] Patent Number: Plant 9,421

[45] Date of Patent: Jan. 9, 1996

[54] HYBRID TEA ROSE PLANT NAMED 'RUICREVI'

[75] Inventor: A. A. Pouw, Hazerswoude, Netherlands

[73] Assignee: De Ruiter's Nieuwe Rozen B.V., Netherlands

[21] Appl. No.: 379,272

[22] Filed: Jan. 27, 1995

[51] Int. Cl.[6] ..... A01H 5/00

[52] U.S. Cl. ..... Plt./14

[58] Field of Search ..... Plt./11, 14, 15, Plt./16

[56] References Cited

U.S. PATENT DOCUMENTS

P.P. 7,622 8/1991 Meilland ..... Plt./15

*Primary Examiner*—Howard J. Locker
*Attorney, Agent, or Firm*—Christie, Parker & Hale

[57] ABSTRACT

A new variety of hybrid tea rose plant having cream colored flowers and suitable for growing under glass.

2 Drawing Sheets

SUMMARY OF THE INVENTION

The present invention realtes to a new and distinct variety of rose plant of the hybrid tea rose class created by crossing as seed and pollen parents two unnamed, unpatented and undistributed seedlings of my creation. The varietal denomination of the new variety is 'Ruicrevi'.

Among the novel characteristics possessed by this new variety which distinguish it from its parents and all other varieties of which I am aware are its attractive cream colored flowers borne on a floriferous plant with long stems and suitable for production of cut flowers under glass. The new variety can be reproduced through propagation by cuttings, grafting, budding and micropropagation.

Asexual reproduction by budding of the new variety as performed in Holland shows that the foregoing and other distinguishing characteristics come true to form and are established and transmitted through succeeding propagations.

BRIEF DESCRIPTION OF ILLUSTRATION

The accompanying illustrations show typical specimens of the vegetative growth and flowers of the new variety in different stages of development depicted in color as nearly true as it is reasonably possible to make the same in a color illustration of this character. Colors may vary depending upon growing conditions under different climate, soil, and cultivation conditions, and phenotypic expression may also vary with light cultural and environmental conditions.

One of the accompanying illustrations shows cut flower form of the new variety to illustrate optimum flower form and the other illustration shows details of the new rose variety in color more nearly correct for the variety.

DESCRIPTION OF THE NEW VARIETY

The following is a detailed description of the new variety, with color terminology in accordance with The Royal Horticultural Society Colour Chart (R.H.S.C.C.) and horticultural terminology in accordance with standard terminology used in UPOV-approved horticultural guidelines. The terminology used in color descriptions herein refers to plate numbers in the aforementioned color chart.

Parentage: Unnamed seedlings as male and female parents.

Class: Hybrid Tea.

As can be seen in the accompanying detailed illustration there is shown a new shoot, 1; compound three, five and seven leaflet leaves, 2, 3 and 4, respectively; a stem, 5; buds, 6 and 7; a flower, 8, about one-third open; and a flower, 9, more fully open. Also shown are flower stems 10, 11 and 12, with reproductive organs displayed. The other illustration shows cut flower form of the new variety.

The following further horticultural description is based on observations made of specimens grown under glass in Holland.

FLOWER

Blooming habit: Nearly continuous; average production about 150 blooms/m$^2$/year.

A. Bud:

(1) *Size.*—Medium, about 5 to 6 cm long and about 3 to 4 cm wide.

(2) *Form.*—Ovate (shape of longitudinal section just before separation of sepals); urn-shaped after sepals part.

(3) *Color.*—As sepals divide, near 158A.

(4) *Sepals.*—Longer than green bud, generally simple; near 137B to 137C.

(5) *Peduncle.*—Long; Aspect — straight; Strength — erect, very strong. Color — medium green, near 139B to 139C.

B. Bloom:

*Flower.*—Large; viewed from above — star — shaped; viewed from side — (a) upper part of fully opened flower, flattened convex; (b) lower part of fully opened flower, flat.

(1) *Size.*—Average size when fully expanded — about 11 cm, stem length about 70 cm.

(2) Borne.—Singly, one to a stem.

(3) *Form.*—High centered, exhibition type, spiral imbricated, outer petals quill to points, inner petals roll under.

(4) *Petalage.*—Fully double, about 30.

(5) *Color.*—When sepals part and petals begin petal top surface appears cream, near 155D to 159D with near 4D to 4C center where petals bunch; petal undersurface near 158A to 158D. Overall tonality from a distance is near white to cream. Color at point of petal attachment is substantially the same as petal.

(6) *Peduncle*—Generally smooth.

(7) *Fragrance*—Slight to none.

c. Petals:
(1) *Texture.*—Crisp.
(2) *Appearance.*— Inside velvety and outside satiny.
(3) *Form and size.*—Broad, medium, some undulation of margin.
(4) *Arrangement.*—Regularly arranged, imbricated.
(5) *Petaloids.*—Several.
(6) *Lasting quality.*—Long-lasting quality on plant and after cutting.

REPRODUCTIVE ORGANS

A. Stamens, filaments and anthers:
*Arrangement and color.*—Regularly arranged around styles; color of filaments — yellow with orange red tips.
B. Pollen:
*Color.*—Deep yellow.
C. Styles: Long, stigma above mouth of receptacle.
D. Stigmas: Positioned below anthers, near 180A.
E. Hip: Pitcher-shaped; large seed vessel at petal fall.

PLANT

A. Form: Narrow, bushy, average disease resistance.
B. Growth: Vigorous.
C. Foliage: Compound 3, 5, and 7 leaflets.
(1) *Size.*—Medium to large.
(2) *Quantity.*—Abundant.
(3) *Color.*—Juvenile foliage — red purple, near 182A, mature leaf color — near 147A.
(4) *Shape.*—Broad oval.
(5) *Texture.*—Upper side is leathery and slight to medium glossy; underside to matte.
(6) *Edge.*—Serrate.
(7) *Serration.*—Ordinary, acuminate apices.
(8) *Leaf stem.*—Color — green, near 137A with brownish cast.
(9) *Stipules.*—Narrow, long, green, distinct auricle.
(10) *Leaflets.*—Cross section — slight convex; medium undulation at margin; terminal leaflet — blade long, 6 to 7 cm long, 5 to 6 cm wide, rounded base.
(11) *Flower pedicel.*—Almost no hairs or prickles.
D. Wood:
(1) *New wood.*—Color — young shoots have medium to strong anthocyanin; coloration — bronze.
(2) *Old wood.*—Color — medium green, near 147B.
E. Prickles (thorns):
(1) *Prickles.*—Present; quantity (main stalk) — ordinary; on laterals from stalk — ordinary; short prickles absent or very few; shape of lower side — concave; Length — average; Color — near 182A to 182B; Position — irregular.

What is claimed is:

1. A new and distinct variety of rose plant of the hybrid tea rose class, substantially as shown and described.

* * * * *

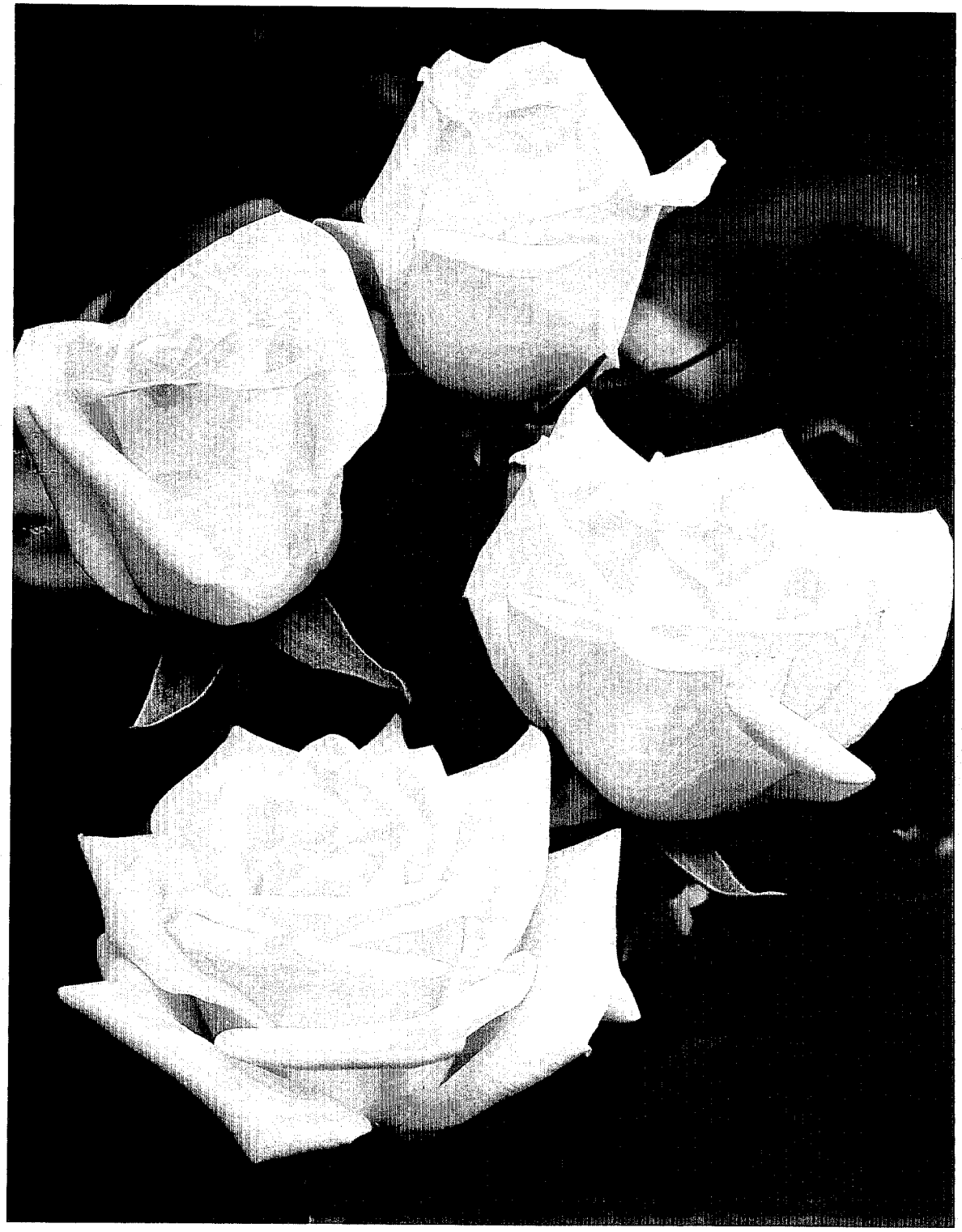

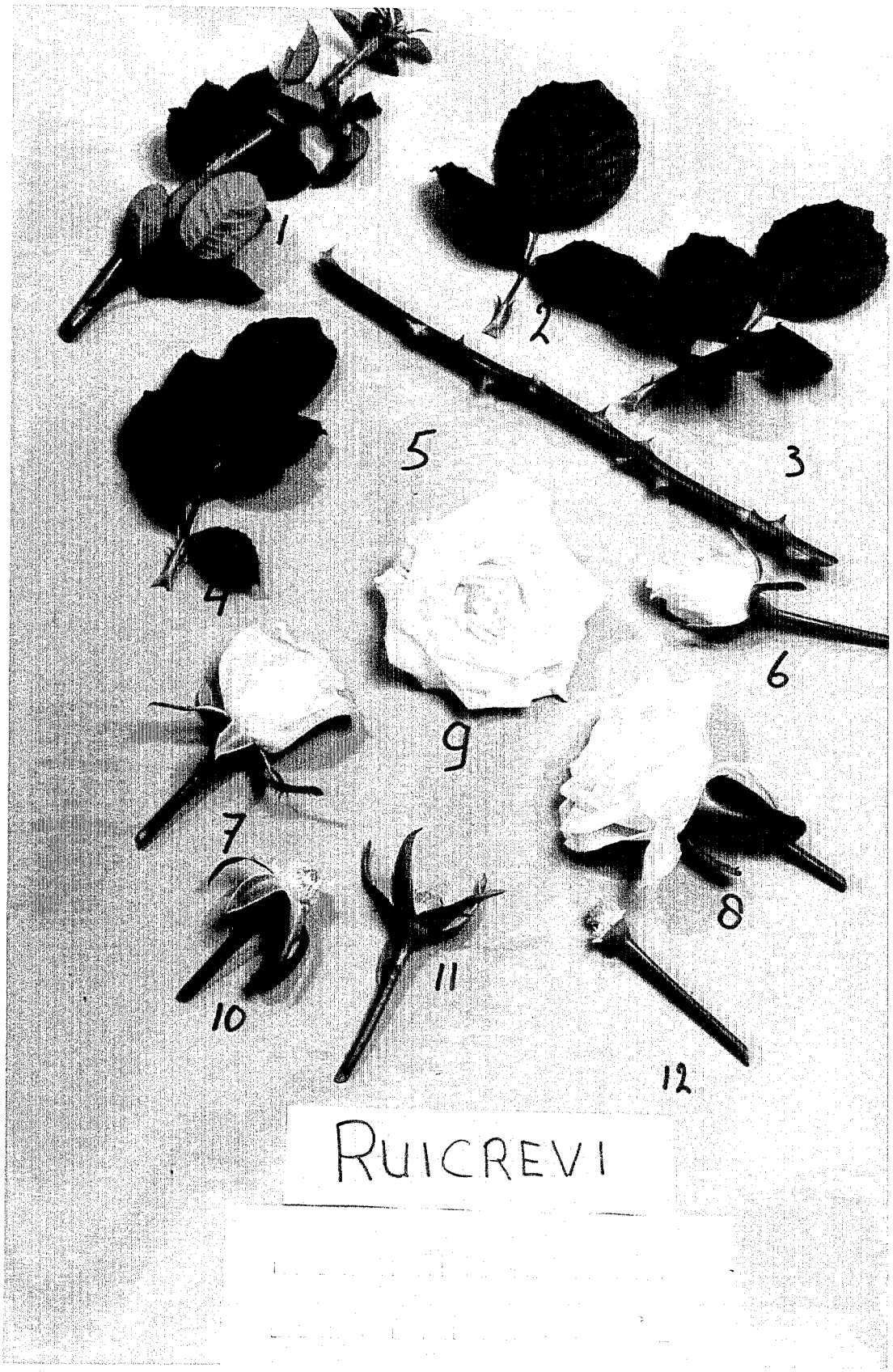
1
2
3
4
5
6
7
8
9
10
11
12
RUICREVI